United States Patent

Wilson et al.

Patent Number: 5,279,297
Date of Patent: Jan. 18, 1994

[54] METHOD AND APPARATUS FOR OXYGEN MAPPING

[75] Inventors: David F. Wilson, Philadelphia, Pa.; Marek Pawlowski, Roslyn Heights, N.Y.

[73] Assignee: Trustees of the University of Pennsylvania, Philadelphia, Pa.

[21] Appl. No.: 763,184

[22] Filed: Sep. 20, 1991

[51] Int. Cl.⁵ ................................................ A61B 5/00
[52] U.S. Cl. .................................... 128/633; 250/458.1
[58] Field of Search ................ 128/633, 635, 654, 664, 128/665; 364/413.1, 413.13; 250/413.13, 458.1

[56] References Cited

U.S. PATENT DOCUMENTS

| | | | |
|---|---|---|---|
| 4,058,732 | 11/1977 | Wieder | 250/461 B |
| 4,541,438 | 9/1985 | Parker et al. | 128/664 |
| 4,910,404 | 3/1990 | Cho et al. | 128/633 |
| 5,095,431 | 3/1992 | Feldman et al. | 364/413.13 |

Primary Examiner—Lee S. Cohen
Assistant Examiner—Marianne Parker
Attorney, Agent, or Firm—Woodcock Washburn Kurtz Mackiewicz & Norris

[57] ABSTRACT

An system for imaging an oxygen-containing animal includes an illuminating light source 10, optical filters 12, a microscope and an associated epifluorescence attachment 16, a long pass cutoff filter 8, a camera 20, a frame grabber 22, a counter timer board 24, a computer 26 and an analog monitor 28. The light from the flash lamp 10 is passed through the optical filters to remove an unwanted portion of the spectrum, and focused on a sample object 14 through the epifluorescence attachment and phosphorescence is observed through the long pass cutoff filter. The images are collected with the camera and the frame grabber is used to digitize and average frames while the timing of the flash and gating of the camera intensifier is controlled by the counter timer board. The frames are displayed on the analog monitor.

20 Claims, 2 Drawing Sheets

METHOD AND APPARATUS FOR OXYGEN MAPPING

Field of the Invention

The present invention generally relates to the field of imaging body portions of animals. More particularly, the present invention is an extension and improvement of the subject matter of U.S. Pat. No. 4,947,850, Aug. 14, 1990, entitled "Method And Apparatus For Imaging An Internal Body Portion Of A Host Animal," which is hereby incorporated by reference into this specification.

BACKGROUND OF THE INVENTION

The present invention is based upon the observation that oxygen can have a quenching effect on the molecular luminescence of various chemical compounds and that this effect may be employed in mapping or imaging oxygen concentrations of body portions of animals. Information about the distribution and concentration of oxygen is extremely useful in that it is indicative of tissue structure, anomalies, defects and diseases. The reader is referred to the above-cited U.S. Pat. No. 4,947,850 for further discussion of the background of the present invention.

SUMMARY OF THE INVENTION

The present invention provides improved methods and apparatus for imaging internal body structures of animals. Methods in accordance with the present invention comprise the steps of: effecting phosphorescence of a body portion of a host animal; detecting, at a plurality of locations, phosphorescence emissions from the body portion; constructing data sets, on the basis of the detected phosphorescence emissions, including decay constants $T_{(x,y)}$ and oxygen pressure or concentration values $pO_{2(x,y)}$; and displaying an image indicative of at least one of the data sets. In the context of the invention, x and y are indices whose values represent respective locations at which the phosphorescence emissions were detected.

A preferred embodiment of the present invention comprises the steps of (1) illuminating the body portion with light at a wavelength and for a duration of time sufficient to effect phosphorescence; (2) delaying for a first prescribed period following effectuation of phosphorescence; (3) detecting emissions from the body portion during a second prescribed period following the delay; (4) repeating steps (1) through (3) a prescribed number of times N to obtain N frames of emissions data; and (5) constructing a composite frame indicative of an average of the N frames.

Further embodiments of the invention may optionally comprise the step of filtering at least one of the frames of emissions data or filtering the composite frame.

In accordance with the invention a background frame may be obtained by collecting image data after a delay of at least about five times a decay constant $T_{(x,y)}$. The background frame may then be subtracted from the composite frame. Further, after subtraction of the background frame, the composite frame may be filtered to remove noise and improve image quality and then stored.

Still other embodiments of the present invention may comprise the steps of repeating at least the first three steps (i.e., the effecting, detecting and constructing steps) to obtain a prescribed number (I) of composite frames, and computing, on the basis of the I composite frames, a frame of decay constants $T_{(x,y)}$ and a frame of oxygen pressure or concentration values $pO_{2(x,y)}$. In addition, the third (constructing) step may comprise determining a data set of initial values $T_{0(x,y)}$ and a data set of correlation coefficients $\rho_{(x,y)}$. Each value $pO_{2(x,y)}$ may be computed from the relationship:

$$T_O/T = 1 + K_Q \cdot T_O \cdot pO_2,$$

where $T_O$ and $K_Q$ are constants determined in calibration experiments.

A preferred imaging method (or system) in accordance with the invention comprises the steps of (or means for): directing light from a light source through at least one optical filter to remove an unwanted portion of the spectrum, focusing the light on a sample object through an epifluorescence attachment to a microscope, observing phosphorescence through a long pass cutoff filter, collecting frames of digital images with a camera, camera intensifier and frame grabber while controlling the timing of the flash lamp and gating of the camera intensifier with a computer and counter timer board, averaging the frames to obtain a composite frame, and displaying the composite frame. Most preferably the light source will comprise a flash lamp with a flash duration of less than 5 μs, the long pass cutoff filter will provide approximately 50% transmission at 630 nm, the camera will comprise a CCD camera, the intensifier will comprise a Xybion intensifier with a red sensitive coating, and the computer will comprise an IBM-PC/AT compatible computer.

In addition to the foregoing methods and apparatus, the inventors also claim, as being within the scope of their invention, computer record media (e.g., magnetic and optical disks, magnetic tapes, etc.) comprising encoded signals for directing an imaging system in imaging a body portion of a host animal. The imaging system should include an illuminating light source, a microscope and an associated epifluorescence attachment, a long pass cutoff filter, a camera, a frame grabber, a counter timer board, a computer and an analog monitor. The encoded signals comprise instructions for directing the system in carrying out the steps of effecting phosphorescence of the body portion; detecting, at a plurality of locations, phosphorescence emissions from the body portion; constructing the following data sets on the basis of the detected phosphorescence emissions: decay constants $T_{(x,y)}$ and oxygen pressure or concentration values $pO_{2(x,y)}$; and displaying an image indicative of at least one of the data sets.

Other features and advantages of the invention are described below in connection with the detailed description of preferred embodiments.

DETAILED DESCRIPTION OF PREFERRED EMBODIMENTS

Figure 1:
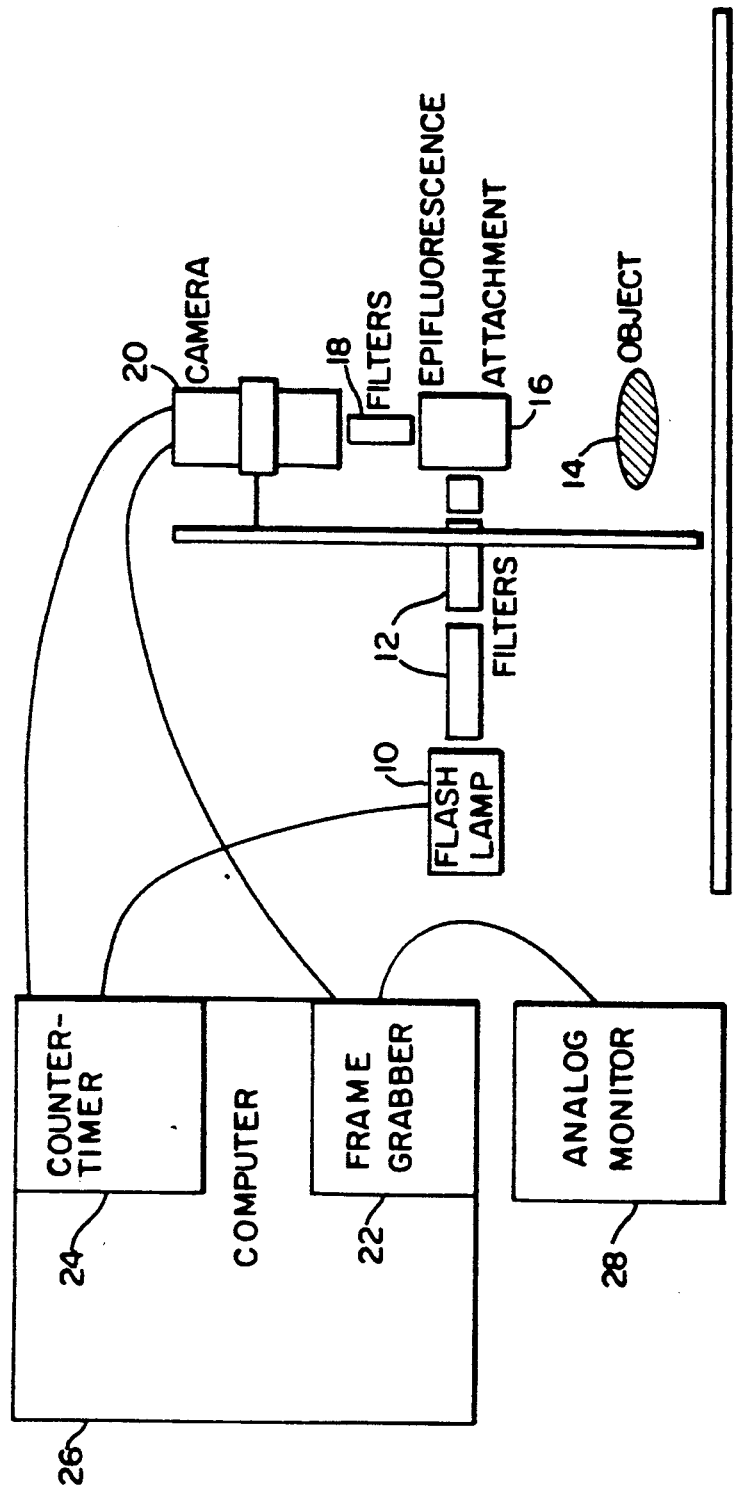
FIG. 1 is a block diagram of one embodiment of an imaging system in accordance with the present invention.

Referring to FIG. 1, a measurement system in accordance with the present invention includes an illuminating light source 10, optical filter(s) 12, a microscope and an associated epifluorescence attachment 16, a long pass cutoff filter 18, a camera 20, a frame grabber 22, a counter timer board 24, a computer 26 and an analog monitor 28. The frame grabber 22 and counter timer board 24 are mounted in the computer 26. In one preferred embodiment the illuminating light source 10 is an EG&G flash lamp with a flash duration of less than 5 $\mu s$; the microscope is a Wild-Leitz Macrozoom microscope; the long pass cutoff filter 18 provides 50% transmission at 630 nm; the camera 20 is a Xybion intensified (gain approximately 18,000) CCD camera with a red sensitive coating on the intensifier and capable of capturing 30 frames per second in its diode storage array; the frame grabber 22 is a Matrox MVP-AT frame grabber; the counter timer board 24 is a CTM-05 board (available from MetraByte Corp., Taunton, Mass.); and the computer 26 is an IBM-PC/AT compatible 80386/16 MHz computer.

According to the present invention, the light from the flash lamp 10 is passed through the optical filters 12, to remove an unwanted portion of the spectrum, and focused on a sample object 14 through the epifluorescence attachment 16; phosphorescence is then observed through the long pass cutoff filter 18. The images are collected with the camera 20 and the frame grabber 22 is used to digitize and average frames while the timing of the flash and gating of the camera intensifier is controlled by the counter timer board 24. The computer 26, operating under the direction of software (not shown) in accordance with the present invention, controls the counter timer board 24, camera intensifier, frame grabber 22 and a computer storage device (not shown).

A concise description of a preferred method of operation is provided below with reference to the flowchart of FIG. 2.

The following list briefly enumerates the basic processes or steps of a method for operating the imaging system of FIG. 1 to obtain an oxygen map of a body portion (labelled "object" in FIG. 1) of a subject:

1. Collection of the image of phosphorescence for a given period of time after illumination with the flash lamp.
   a) Preparation of the camera 20 (including clearing of the camera storage array and suppression of the image output).
   b) Firing of the flash lamp 10.
   c) Setting the delay and gating of the camera intensifier (i.e., setting duration of delay and duration the intensifier is on).
   d) Triggering transfer of the image to the frame grabber 22. This sequence is repeated as many times as the operator requests, typically from 2 to 32 times. The images are averaged in real time.
   e) Transfer of the averaged image to a computer storage device.
2. Display of the phosphorescence intensity images during the above experimental protocol.

The image is displayed on a monitor for observation by the operator at the end of collection of the averaged phosphorescence intensity image for each delay time. Each image is displayed until the next image has been collected.

3. Collection of the sequence of images with different delay times after the flash.

The steps of paragraph 1 (or process 1) above are repeated with the counter-timer board 24 programmed for different delays after the flash according to the sequence requested by the operator. The result is a series of images stored on the computer storage device, each for a different delay time after the flash. A typical sequence of images might consist of delays after the flash of 20 $\mu s$, 40 $\mu s$, 80 $\mu s$, 160 $\mu s$, 300 $\mu s$, 600 $\mu s$ and 2,500 $\mu s$, each with a gate width (period of time the intensifier is on) of 2,500 $\mu s$.

4. Analysis of the data:
   a) The images are placed in a computer memory and each is smoothed with a filter to reduce any noise.
   b) The background intensity image is subtracted from all the other images. The background is an image collected with a delay of more than 5 times the phosphorescence lifetime, when the phosphorescence emission is negligible in comparison to the emissions corresponding to the delay periods of interest (e.g., a delay of 2,500 $\mu s$ may be used as a background when the lifetimes expected to be measured are from 60 to 600 $\mu s$).
   c) The phosphorescence lifetimes are calculated for each pixel of the image array by a linear regression best fit to a single exponential (i.e., the parameters of an exponentially decaying function or curve are derived). This facilitates the generation of two new two-dimensional maps, one of the initial (zero delay) phosphorescence intensities and one of the phosphorescence lifetimes. The correlation coefficient for the fit of the data to the single exponential is calculated for each lifetime and these are stored as an additional two-dimensional map. Routines for fitting to multiexponential decay may also be included.
   d) The oxygen pressure map is calculated from the phosphorescence lifetime map and the values for $k_Q$ and $T_O$ (determined independently in calibration experiments) using the Stern-Volmer relationship:

$$T_O/T = 1 + k_Q*T_O*pO_2,$$

where $T_O$ (also called "$\tau_O$") represents the lifetime in the absence of oxygen, $k_Q$ represents the quenching constant for oxygen and $pO_2$ represents the oxygen pressure for a lifetime of T. It is apparent that the above relationship holds whether $pO_2$ represents oxygen pressure or oxygen concentration, as each one of those parameters is proportional to the other.

5. Processing of the phosphorescence intensity data:

Data processing software was written in C language using the Watcom C Professional version 8.0, 32 bit, 386 protected mode compiler (available from Watcom Systems, Inc., Waterloo, Ontario, Canada). To operate on large amounts of data, the C language program works under an OS/386 Developers kit version 2.1.05 DOS extender operating system (available from ERGO Computing Inc., Peabody, Mass.). The phosphorescence lifetimes and the correlation coefficients are calculated using least squares linear regression. There are additional image processing options designed to optimize the data presentation, including filters for smoothing and edge enhancement, various graphical display options, and pseudocolor. The phosphorescence images and two-dimensional maps are displayed and/or hardcopied by a printer, in accordance with the operator's wishes.

Figure 2:
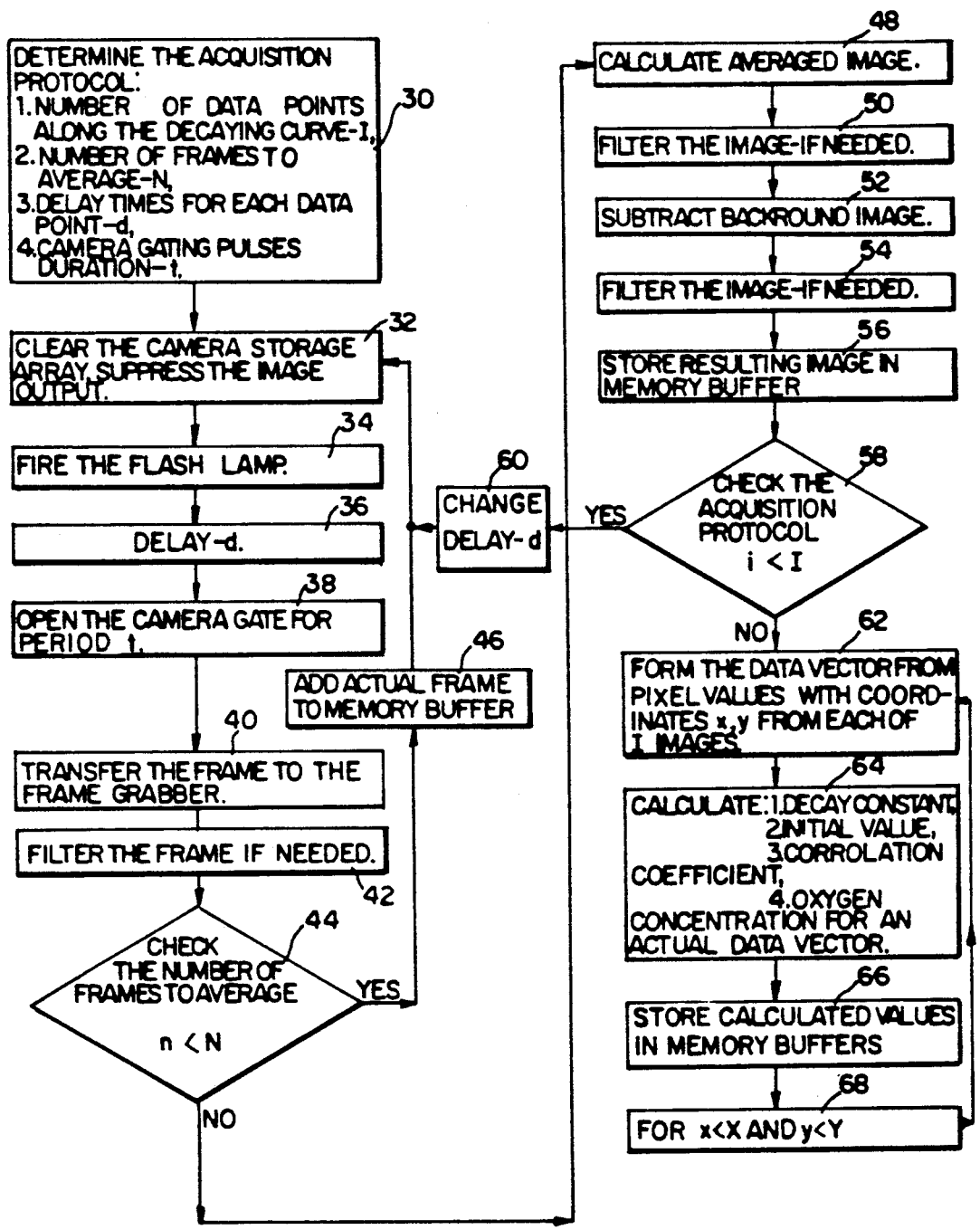
FIG. 2 is a flowchart of one method for oxygen mapping or imaging in accordance with the present invention.

Referring now to the flowchart of FIG. 2, the imaging system of FIG. 1 may be programmed in accordance with the present invention to perform the processes indicated in the respective blocks.

First, as shown in block 30, the computer determines the desired acquisition protocol. That process includes determining the desired number of data points (I) along each decaying luminescence curve (i.e., the number of images to collect), determining the number of frames (N) to average for each image, determining the delay period (d) and determining the duration (t) of each camera gating pulse.

The camera storage array is then cleared and the image output is suppressed (block 32). Next the flashlamp is fired (block 34). The system then waits for the prescribed delay period d (block 36). Next the camera gate is opened for the prescribed period t (block 38). A frame of data is then transferred from the camera to the frame grabber (block 40). Then, if necessary, the captured data frame is filtered (block 42).

At decision block 44 the computer determines whether the number of frames captured (n), which is one after the first pass through the loop, is less than N (the specified number of frames to average). If n is less than N, the program adds the captured frame to a memory buffer associated with the computer and then loops to block 32. If n is equal to or greater than N a composite frame is constructed from an average of corresponding pixels of the N captured frames (block 48). If necessary, the composite frame is filtered to remove noise or otherwise improve the quality of the data (block 50). At block 52 the previously-obtained background data is subtracted from the composite image. The resulting frame after subtraction of the background frame is then filtered as before if necessary (block 54) and stored in memory (block 56). The computer then determines whether the number of data points collected (i) is less than the prescribed number of points (or images) I (block 58). The program then changes the delay d (e.g., from 20 $\mu$s to 40 $\mu$s, from 40 $\mu$s to 80 $\mu$s, etc.) (block 60) and loops to block 32 if i is less than I; otherwise it proceeds to block 62 and forms data vectors corresponding to the pixels of the I frames of data with indices x, y.

At block 64 the computer calculates decay constants $T_{(x,y)}$, initial values $T_{O(x,y)}$ correlation coefficients $\rho_{(x,y)}$ and oxygen pressure or concentration values $pO_{2(x,y)}$ for that data vector. The calculated values are then stored in memory (block 66). At block 68 the computer determines whether x and y are less than their respective predefined maximum values (X, Y) and, if so, loops to block 62 to process the remaining pixels. Once the pressure map is obtained a representative image may be displayed using conventional image processing methods. That image may be advantageously employed in the detection of tissue anomalies, defects and diseases.

What is claimed:

1. A method for imaging a body portion of a host animal, comprising the steps of:
   (a) effecting phosphorescence of said body portion;
   (b) detecting, at a plurality of locations phosphorescence emissions from said body portion;
   (c) constructing the following data sets on the basis of the detected phosphorescence emissions: decay constants $T_{(x,y)}$ and oxygen pressure or concentration values $pO_{2(x,y)}$, wherein x and y are indices whose values represent respective locations at which the phosphorescence emissions were detected; and
   (d) displaying an image indicative of at least one of said data sets,
   wherein steps (a) and (b) comprise the following substeps:
   (1) illuminating said body portion with light at a wavelength and for a duration of time sufficient to effect phosphorescence;
   (2) delaying for a first prescribed period following effectuation of phosphorescence;
   (3) detecting said emissions during a second prescribed period following said delay;
   (4) repeating said substeps (1) through (3) a prescribed number of times N, thereby obtaining N frames of emissions data; and
   (5) constructing a composite frame indicative of an average of said N frames.

2. The method recited in claim 1, further comprising the step of filtering at least one of said frames of emissions data.

3. The method recited in claim 1, further comprising the step of filtering said composite frame.

4. The method of claim 1, further comprising the step of obtaining a background frame by collecting image data after a delay of at least about five times a decay constant $T_{(x,y)}$.

5. The method recited in claim 4, further comprising the step of subtracting said background frame from said composite frame.

6. The method recited in claim 5, further comprising the step of filtering said composite frame after subtracting said background frame.

7. The method recited in claim 5, further comprising the step of storing said composite frame after subtracting said background frame.

8. The method recited in claim 7, further comprising the steps of:
   (e) repeating at least steps (a) through (c) to obtain a prescribed number (I) of composite frames; and
   (f) computing, on the basis of said I composite frames, a frame of decay constants $T_{(x,y)}$ and a frame of oxygen pressure or concentration values $pO_{2(x,y)}$.

9. The method recited in claim 8, wherein step (c) further comprises the step of determining a data set of calibration values $T_{O(x,y)}$ and a data set of correlation coefficients $\rho_{(x,y)}$, wherein $T_{O(x,y)}$ represents constants determined in calibration experiments and each value $pO_{2(x,y)}$ is determinable from the relationship: $T_{O(x,y)}/T_{(x,y)} = 1 + K_Q * T_{O(x,y)} * pO_{2(x,y)}$, wherein $K_Q$ is a constant.

10. An apparatus for imaging a body portion of a host animal, comprising:
   (a) means for effecting phosphorescence of said body portion;
   (b) means for detecting, at a plurality of locations, phosphorescence emissions from said body portion;
   (c) means for determining the following data sets on the basis of the detected phosphorescence emissions: decay constants $T_{(x,y)}$ and oxygen pressure or concentration values $pO_{2(x,y)}$, wherein x and y are indices whose values represent respective locations at which the phosphorescence emissions were detected; and
   (d) means for displaying an image indicative of at least one of said data sets, wherein means (a) and (b) comprise:
   means for (1) illuminating said body portion with light at a wavelength and for a duration of time sufficient to effect phosphorescence;

means for (2) delaying for a first prescribed period following effectuation of phosphorescence;

means for (3) detecting emissions from said body portion during a second prescribed period following said delay;

means for (4) repeating said steps (1) through (3) a prescribed number of times N and thereby obtaining N frames of emissions data; and means for (5) constructing a composite frame indicative of an average of said N frames.

11. The apparatus recited in claim 10, further comprising means for filtering at least one of said frames of emissions data.

12. The apparatus recited in claim 10, further comprising means for filtering said composite frame.

13. The apparatus of claim 10, further comprising means for obtaining a background frame by collecting image data after a delay of at least about five times a decay constant $T_{(x,y)}$.

14. The apparatus recited in claim 13, further comprising means for subtracting said background frame from said composite frame.

15. The apparatus of claim 14, further comprising means for filtering said composite frame after subtracting said background frame.

16. The apparatus recited in claim 14, further comprising means for storing said composite frame after subtracting said background frame.

17. The apparatus recited in claim 16, further comprising:

(e) means for obtaining a prescribed number (I) of composite frames; and (f) means for computing, on the basis of said I composite frames, a frame of decay constants $T_{(x,y)}$ and a frame of oxygen pressure or concentration values $pO_{2(x,y)}$.

18. The apparatus recited in claim 19, wherein means (c) further comprises means for determining a data set of calibration values $T_{O(x,y)}$ and a data set of correlation coefficients $\rho_{(x,y)}$, wherein $T_{O(x,y)}$ represents constants and each value $pO_{2(x,y)}$ is determinable from the relationship: $T_{O(x,y)}/T_{(x,y)} = 1 + K_Q * T_{O(x,y)} * pO_{2(x,y)}$, wherein $K_Q$ is a constant.

19. An imaging method, comprising the steps of directing light from a light source through at least one optical filter to remove an unwanted portion of the light, focusing said filtered light on a sample object through an epifluorescence attachment to a microscope, observing phosphorescence of said object through a long pass cutoff filter, collecting frames of digital images of said object with a camera, camera intensifier and frame grabber while controlling the light source and gating of the camera intensifier with a computer, averaging said frames to obtain a composite frame, and displaying the composite frame.

20. The method recited in claim 19, wherein:

the step of directing light from a light source through at least one optical filter comprises directing a light flash with a flash duration of less than 5 μs through at least one optical filter;

the long pass cutoff filter provides approximately 50% transmission at 630 nm;

the camera comprises a CCD camera and the intensifier comprises a Xybion intensifier with a red sensitive coating; and the computer comprises an IBM-PC/AT compatible computer.

* * * * *